United States Patent [19]
Nöldner et al.

[11] Patent Number: 5,550,129
[45] Date of Patent: Aug. 27, 1996

[54] BENZOPYRANONES, PROCESSES FOR THEIR PREPARATION AND THEIR USE

[75] Inventors: Michael Nöldner, Eggenstein; Shyam S. Chatterjee; Hermann Hauer, both of Karlsruhe, all of Germany

[73] Assignee: Willmar Schwabe GmbH & Co., Karlshruhe, Germany

[21] Appl. No.: 411,621

[22] PCT Filed: Oct. 6, 1993

[86] PCT No.: PCT/EP93/02742

§ 371 Date: Apr. 5, 1995

§ 102(e) Date: Apr. 5, 1995

[87] PCT Pub. No.: WO94/08985

PCT Pub. Date: Apr. 28, 1994

[30] Foreign Application Priority Data

Oct. 8, 1992 [DE] Germany ............................ 42 33 963.4

[51] Int. Cl.⁶ ................... A61K 31/495; A61K 31/445; C07D 409/00; C07D 211/68
[52] U.S. Cl. ................. 514/253; 514/320; 544/295; 544/333; 544/360; 544/376; 546/193; 546/196
[58] Field of Search ...................... 544/295, 333, 544/360, 376; 546/193, 196; 514/253, 320

[56] References Cited

U.S. PATENT DOCUMENTS

| | | | |
|---|---|---|---|
| 3,538,098 | 11/1970 | Beyerle et al. | 514/253 |
| 3,930,003 | 12/1975 | Becker et al. | 514/253 |

FOREIGN PATENT DOCUMENTS

| | | |
|---|---|---|
| 1670468 | 3/1971 | Germany. |
| 2448257 | 4/1976 | Germany. |

OTHER PUBLICATIONS

Vyas et al, J. Indian Chem. Soc. vol. 67, 1990, pp. 482–484.

*Primary Examiner*—Cecilia Tsang
*Attorney, Agent, or Firm*—Frost & Jacobs

[57] ABSTRACT

Described are 2H-1-benzopyran-2-ones (coumarin derivates) of general formula (I),

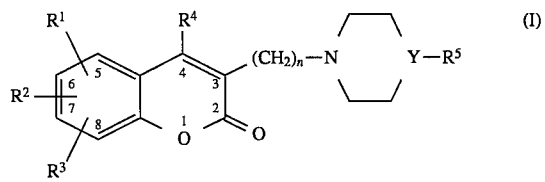

wherein $R^1$ is a hydroxyl group, a lower-alkoxy group, a cycloalkoxy group with 4 to 6 C-atoms or the alkyl- or arylsulphonyloxy group $R^6$—$SO_2O$—;

$R^2$ and $R^3$, independently of each other, are hydrogen atoms, hydroxyl groups, lower-alkoxy groups or cycloalkoxy groups with 4 to 6 C-atoms;

$R^4$ is a hydrogen atom, a lower-alkyl group with 1 to 4 C-atoms or a phenyl group;

Y is a nitrogen atom, a CH group or a COH group;

$R^5$ is a phenyl, naphtyl, pyridinyl or pyrimidinyl group which may optionally be substituted by one or two $C_1$–$C_5$ alkyl groups, by one or two halogen atoms, by a halogen and $C_1$–$C_5$ alkyl together, by perfluoroalkyl with 1 to 3 C-atoms, by $C_1$–$C_5$ alkoxy, by hydroxy, by methylenedioxy or by nitro;

$R^6$ is a lower-alkyl group, a cycloalkyl group with 4 to 6 C-atoms or a phenyl group which may optionally be substituted by one or two $C_1$–$C_5$ alkyl groups, by one or two halogen atoms, or by perfluoroalkyl with 1 to 3 C-atoms; and n= 1 to 4;

plus their addition compounds with physiologically tolerated acids.

Also described are methods of preparing these compounds, novel intermediates in their preparation and methods of preparing such intermediates. The novel coumarin derivatives described possess a neuroprotective and psychopharmacological action. The invention also concerns pharmaceuticals containing these compounds.

3 Claims, No Drawings

BENZOPYRANONES, PROCESSES FOR THEIR PREPARATION AND THEIR USE

This application is a 371 of PCT/EP93/02742, filed Oct. 6, 1993.

The invention relates to benzopyranones whose basic structure can be derived from coumarin, processes for the preparation of these compounds, including the resultant reactive intermediate products, as well as drugs that contain these compounds.

The central nervous system (CNS) of mammals has high concentrations of excitatory amino acids (EAA) such as glutamate, aspartate and homocysteate, which act as neurotransmitters that cooperate with specific receptors.

The three best characterised receptor types are the N-methyl-D-aspartate- (NMDA), kainate- (KA) and quisqualate- (QA) receptors named after their selective agonists. All three receptors can be activated by glutamate and aspartate. It is known that, as a result of cerebral ischaemia, glutamate is released in relatively large amounts, and, among other things, binds to the NMDA receptor complex and leads to an enhanced calcium inflow as well as to an increased release of intracellular calcium in the neuronal cells.

The NMDA receptor complex includes, inter alia, binding sites for glutamate, glycine, phencyclidine, $Mg^{2+}$ and $Zn^{2+}$. Since a number of pharmacological results indicate that modulators of the NMDA receptor-mediated neurotransmission can influence the NMDA-mediated cytotoxicity, various selective NMDA antagonists have already been investigated with regard to their possible neuroprotective action (see G. L. Coilingridge, R. A. J. Lester: "Excitatory Amino Acid Receptors in the Vertebrate Central Nervous System", Pharmacol. Rev. 40, No. 2, p. 143–210 (1989); L. Turski: "N-methyl-D-aspartate-receptor complex", Arzneim. - Forsch. Drug. Res. 40 (I), No. 5, p. 511–514 (1990)). On account of undesirable side effects of the known NMDA antagonists there is furthermore an urgent need to provide new compounds with a NMDA-antagonist action that exhibit fewer side effects or have a different activity spectrum.

The object of the invention is accordingly to provide new compounds that have the lowest possible toxicity but still retain a NMDA-antagonist action and which can be used as active drug constituents, particularly in the treatment of chronic neurodegenerative diseases, in order to prevent or at least reduce neurodegeneration in the CNS caused by ischaemia/trauma or other pathological changes, and the occurrence of convulsions.

This object is achieved by the provision of the compounds and process according to the invention as well as by the use of these compounds as neuroprotective, anti-convulsive and anti-epileptic drugs. The compounds according to the invention in addition also exhibit remarkable anti-depressive, nootropic, antipsychotic and anxiolytic properties.

The object of the invention are accordingly:
2H-1-benzopyran-2-ones of the general formula I,

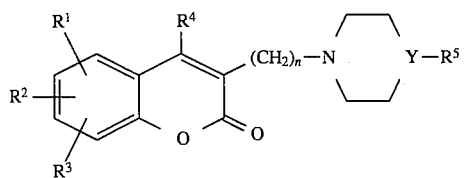

in which $R^1$ is a hydroxy radical, an alkoxy radical with 1 to 5 C atoms, a cycloalkoxy radical with 4 to 6 C atoms, or an alkyl- or arylsulphonyloxy radical $R^6$—$SO_2O$—, $R^2$ and $R^3$ are, independently of one another, hydrogen atoms, hydroxy radicals, alkoxy radicals with 1 to 4 C atoms, or cycloalkoxy radicals with 4 to 6 C atoms, $R^4$ is a hydrogen atom, an alkyl group with 1 to 4 C atoms, or a phenyl radical, Y is a nitrogen atom, a CH group or a COH group, $R^5$ is a phenyl, naphthyl, pyridinyl or pyrimidinyl radical, which is optionally substituted with in each case one or two $C_1$-$C_5$ alkyl groups, with in each case one or two halogen atoms, with halogen and simultaneously $C_1$-$C_5$ alkyl, with perfluoroalkyl with 1 to 3 C atoms, $C_1$-$C_5$ alkoxy, hydroxy, methylenedioxy or nitro, $R^6$ is an alkyl radical with 1 to 5 C atoms, a cycloalkyl radical with 4 to 6 C atoms or a phenyl radical, which is optionally substituted with in each case one or two $C_1$-$C_5$ alkyl groups, with in each case one or two halogen atoms or with perfluoroalkyl with 1 to 3 C atoms, and n is an integer from 1 to 4, as well as their addition compounds with physiologically compatible acids, with the exception however of 7,8-dimethoxy- 4-methyl-3-[(4-phenyl-1-piperazinyl)methyl]-2H-1-benzopyran-2one.

The compounds according to the invention are new. The compound 7,8-dimethoxy-4-methyl-3-[ (4-phenyl-1-piperazinyl)methyl] - 2H-1-benzopyran-2-one, is already known, but has been tested only for its antibacterial action (R. Vyas, S. Bapat, R. H. Mehta, J. Indian Chem. Soc..67, No. 6, p. 482–484 (1990)).

Furthermore, compounds are known in which the coumarin radical and the piperazine radical are joined by an optionally O-acylated 2-hydroxypropylene chain (DE-C3-1668877). In DE-A- 1670395, DE-A-1670465 and DE-A-1670468 compounds are described in which the piperazine nitrogen carries a substituted benzoyloxyalkyl radical. Structurally even further remote from the compounds according to the invention of the general formula I are substituted 7-(aminocarbonylamino)coumarin derivatives (DE-A-2108185, DE-A-2530405 and DE-A-2543945). In all these patent specifications only a coronary-dilatory activity of the compounds claimed therein is mentioned.

Further known compounds are 7-(aminothiocarbonylamino)coumarin derivatives with coronary-dilatory and, in some cases, additional analgesic, sedative and antiinflammatory activity (DE-A-1-2448257). In addition sulphonic acid esters of hydroxycoumarins are known, which however do not contain piperazine or piperidine radicals and are known to have only an antidepressive action (EP-B-111746).

With regard to this state of the art it was surprising and in no way foreseeable by the person skilled in the art that the compounds according to the invention of the general formula I have a NMDA-antagonistic and neuroprotective action.

Preferred compounds according to the invention of the general formula I are those in which $R^1$ is a hydroxy, methoxy, ethoxy, propyloxy or ethanesulphonyloxy radical, $R^2$ and $R^3$ are, independently of one another, hydrogen atoms, hydroxy or alkoxy radicals with 1 to 3 C atoms, $R^4$ is a methyl group, Y is a nitrogen atom, a CH group or a COH group, $R^5$ is a phenyl radical optionally substituted by hydroxy, methoxy, ethoxy, methyl, fluorine or trifluoromethyl, n= 2, as well as their addition compounds with physiologically compatible acids.

In the process according to the invention for preparing the compounds of the general formula I a compound of the general formula II,

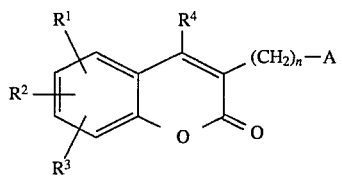

in which R1 to R4 and n have the above meanings and A is a leaving group which is selected from chlorine, bromine, iodine, alkylsulphonyloxy, trifluoromethanesulphonyloxy, phenylsulphonyloxy optionally substituted by alkyl, nitro or halogen, is reacted with a compound of the general formula III

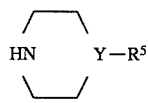

in which Y and $R^5$ have the above meanings, in which connection the compound of the general formula III may also be present in the form of its hydrochloride or another acid addition salt. Afterwards the products obtained are optionally converted into their physiologically compatible acid addition compounds.

The reactions are carried out in a manner known per se. For example, the reaction of 3-(2-bromomethyl)-4-methyl-6,7-dimethoxy-2H-1-benzopyran-2-one with 1-(2-hydroxyethyl)piperazine is described in DE-A-1670468. In order to bind the resultant acid HA, wherein A is one of the leaving groups defined above, these reactions take place in the presence of a base, for example an alkali or alkaline earth metal carbonate, bicarbonate, hydride, alcoholate, hydroxide or a tertiary amine, alkali metal carbonates and bicarbonates preferably being used. It is also possible to use an excess of the reactant III as base. The reactions are advantageously carried out in the presence of solvents inert with respect to the reactants. Solvents particularly suitable for this purpose are alkanols, aromatic solvents such as toluene, xylene, chlorobenzene, etc., or dipolar aprotic solvents such as aliphatic or cycloaliphatic ethers, carboxylic acid dialkylamides, tetraalkyl ureas, ketones and sulphoxides. Alkanols with 1 to 5 C atoms and dimethylformamide are preferred. 0.02 to 0.5 equivalent of an alkali or alkaline earth metal iodide, preferably 0.05 to 0.2 equivalent of potassium iodide, may optionally be added as catalyst. The reaction may be carried out at a temperature between room temperature and 130° C., but preferably between room temperature and 100° C., or, in the case of low boiling point solvents, at a temperature close to the boiling point. Oxidative byproducts are avoided by operating under a protective gas atmosphere, for example nitrogen or argon.

The reactions are carried out under normal pressure or in closed vessels at pressures up to about 107 Pa (100 bar). The preparation of those compounds of the general formula I in which $R^1$ is an alkyl or arylsulphonyloxy radical can also be carried out by reacting the corresponding compound of the general formula I, in which $R^1$ is a hydroxy radical, with a sulphonic acid halide. To this end the alcohol of the general formula I is reacted in a manner known per se with a sulphonic acid halide $R^6SO_2Hal$ where $R^6$ is as defined above. Suitable solvents include, e.g., aromatic compounds such as toluene, xylene, etc., or dipolar aprotic solvents such as aliphatic or cycloaliphatic ethers, carboxylic acid dialkylamides, tetraalkyl ureas, ketones, sulphoxides and halogenated alkanes. Water or lower alcohols are however preferably used. A suitable base, for example an alkali or alkaline earth metal carbonate or a tertiary or aromatic amine, but preferably an alkali or alkaline earth metal hydroxide, is used to bind the hydrohalic acid that is formed. The reaction temperature may be between –30° C. and +80° C., but is preferably between 0° C. and +50° C. Oxidative byproducts can be avoided by operating under a protective gas atmosphere, for example nitrogen or argon.

The reactive intermediate products of the general formula II

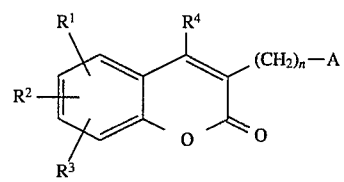

required for the preparation of the compounds according to the invention of the general formula I, in which $R^1$ to $R^4$ and n have the meanings given above and A is a leaving group selected from chlorine, bromine, iodine, alkylsulphonyloxy, trifluoromethylsulphonyloxy, or phenylsulphonyloxy optionally substituted with alkyl, nitro or halogen, are obtained from the corresponding alcohols of the general formula IV

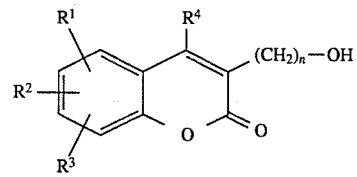

To this end an alcohol of the general formula IV is reacted in a manner known per se a) Either with an acid halide, for example thionyl chloride, thionyl bromide, phosphorus oxychloride, etc., or with an acid such as hydrobromic or hydroiodic acid, halides of the general formula II being obtained, or b) With a sulphonic acid chloride, for example with alkyl sulphonyl or trifluoromethylsulphonyl chloride or with phenylsulphonyl chloride optionally substituted by alkyl, nitro or halogen, sulphonates of the general formula II being obtained.

The reactions under a) are carried out in a solvent inert to the reactants, but preferably in excess acid halide as solvent. In the reactions under b) solvents inert to the reactants are likewise used. Particularly suitable for this purpose are aromatic solvents such as toluene, xylene, etc., or dipolar aprotic solvents such as aliphatic or cycloaliphatic ethers, carboxylic acid dialkylamides, tetraalkyl ureas, ketones, sulphoxides and halogenated alkanes. Preferred solvents in the case of b) are halogenated alkanes such as chloroform or dichloromethane. In addition, with b) a suitable base, for example an alkali or alkaline earth metal carbonate or a tertiary or aromatic amine, is added to bind the hydrohalic acid that is formed, tertiary amines such as triethylamine preferably being used for this purpose. With both a) and b) the reaction temperature may be between –30° C. and +80° C., but is preferably between 0° C. and +50° C. Oxidative byproducts can be avoided by operating under a protective gas atmosphere, for example nitrogen or argon.

Intermediate products of the general formula II in which $R^1$ is an alkyl- or arylsulphonyloxy radical may be prepared from the corresponding compound of the general formula II in which $R^1$ is a hydroxy radical. For this purpose the said compound is reacted with a sulphonic acid halide as described above in the corresponding reaction of the end products of the general formula I.

The intermediate products IV are prepared from the appropriately substituted phenols V

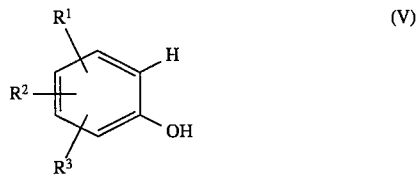

wherein $R^1$, $R^2$ and $R^3$ have the aforementioned meanings. If one or more of the radicals $R^1$, $R^2$ and $R^3$ is a hydroxy group, these hydroxy groups can be alkylated after the cyclisation reaction described in more detail hereinafter.

In order to prepare the intermediate products IV the phenols of the general formula V are reacted in a manner known per se in the presence of an acid catalyst with β-ketocarboxylic acid esters of the general formula VI,

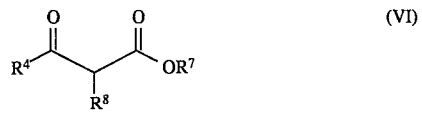

in which $R^4$ has the above meaning, $R^7$ is a lower alkyl radical and $R^8$ is a hydroxyalkylene radical $(CH_2)_nOH$, and/or $R^7$ and $R^8$ together form an alkylene chain $(CH_2)_n$, where n is as defined above. As acid catalysts mineral acids or Lewis acids are used without solvents or in solvents inert with respect to the reaction, e.g. alcohols or glacial acetic acid, preferably 50% to 100% sulphuric acid without any further solvent.

The reaction is carried out at 0° C. to 60° C. preferably at 0° C. to room temperature.

The preliminary products II and IV insofar as they are new, are also the object of the invention.

The object of the invention are in addition drugs that contain as active constituent one or more of the compounds according to the invention of the general formula I as well as optionally, in addition, pharmacologically inert excipients such as water, vegetable oils, polyethylene glycols, glycerol esters, gelatins, carbohydrates such as lactose or starch, magnesium stearate, talc, Vaseline®, preservatives, wetting agents, emulsifiers, physiologically harmless salts, buffer substances, pigments, dyes, flavouring and aroma substances. The choice of accompanying substances depends on the desired form of application, e.g. tablets, dragees, juices, ampoules, suppositories, ointments or sprays. The compounds according to the invention may also be applied mixed with other known active constituents.

The compounds according to the invention, the processes for their preparation as well as the pharmacological experimental results are described in more detail in the following examples.

The abreviation TBME used in the following text denotes tert.-butylmethyl ether.

1. EXAMPLES 1 TO 25 FOR END PRODUCTS OF THE GENERAL FORMULA I

The following processes were used to prepare the compounds described in more detail in the following Examples 1 to 25:

Process A: The (methanesulphonyloxy)alkyl- or chloroalkyl-2H- 1-benzopyran-2-one of the general formula II appropriately substituted with $R^1$ to $R^4$ is stirred with 1.0 to 1.2 equivalents of the desired piperidine or piperazine substituted with $R^5$ of the general formula III in the form of the base or hydrochloride, with 1.5 to 3 equivalents of potassium bicarbonate and with 0.1 to 0.4 equivalent of potassium iodide in dimethylformamide for 3 hours to 70 days under nitrogen at 50°–70° C. The solvent is removed under reduced pressure, the reaction product is taken up in ethyl acetate/water or chloroform/water (if some of the product does not dissolve it can be immediately removed by suction), washed with water, dried over sodium sulphate, the solvent is removed once more, and the product is purified by recrystallisation or by column chromatography over silica gel.

Process B: The (methanesulphonyloxy)alkyl- or chloroalkyl-2H- 1-benzopyran-2-one of the general formula II appropriately substituted with $R^1$ to $R^4$ is stirred with 2.0 to 2.7 equivalents of the desired piperidine or piperazine substituted with $R^5$ of the general formula III and with 0.1 to 0.2 equivalent of potassium iodide in dimethylformamide for 15 hours to 7 days under nitrogen at 40° to 90° C. The solvent is removed under reduced pressure and the reaction product is taken up in chloroform or ethyl acetate. If the product does not occur in crystalline form and can be suction filtered, it is optionally washed with dilute sodium hydroxide and with water, dried over sodium sulphate, and the solvent is removed once more. The product is purified by recrystallisation or by column chromatography over silica gel.

Process C: One equivalent of fumaric acid, dissolved in ethanol or isopropanol, is added to a solution of the base in ethanol, isopropanol, 2-butanone or chloroform. The fumarate is formed as crystals immediately or after concentration by evaporation and is recrystallised. Unless stated otherwise in the examples, 1.0 $C_4H_4O_4$ is added in each case.

EXAMPLE 1

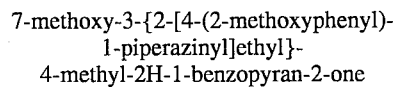

7-methoxy-3-{2-[4-(2-methoxyphenyl)-1-piperazinyl]ethyl}-4-methyl-2H-1-benzopyran-2-one Process A; starting materials: 3-[2-(methanesulphonyloxy)ethyl]- 7-methoxy-4-methyl-2H- 1-benzopyran-2-one (Example 26) and 1-(2-methoxyphenyl)piperazine; yield 29%; m.p. 129°–130° C. (from ethanol/TBME).

Fumarate (x 0.5 $C_4H_4O_4$): process C; yield 97%; m.p. 182°–185° C. (from ethanol).

EXAMPLE 2

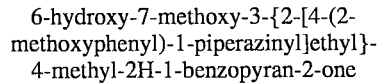

6-hydroxy-7-methoxy-3-{2-[4-(2-methoxyphenyl)-1-piperazinyl]ethyl}-4-methyl-2H-1-benzopyran-2-one Process A; starting materials: 3-(2-chloroethyl)-6-hydroxy- 7-methoxy-4-methyl-2H-1-benzopyran-2-one (Example 27) and 1-(2-methoxyphenyl)piperazine; yield 14%; m.p. 235°–237° C. (from ethanol/chloroform).

EXAMPLE 3:

6,7-dimethoxy-4-methyl-3-[ 2-(4-phenyl-1-piperazinyl)ethyl] -2H-1-benzopyran-2-one Process B; starting materials: 3-[ 2-methanesulphonyloxy)ethyl] - 6,7-dimethoxy-4-methyl-2H- 1-benzopyran-2-one (Example 28) and 1-phenylpiperazine; yield 43%; m.p. 169°–172° C. (from isopropanol).

Fumarate (x 0.5 $C_4H_4O_4$): process C; yield 93%; m.p. 214°–219° C. (from isopropanol).

EXAMPLE 4

6,7-dimethoxy-3-{2-[4-(2-methoxyphenyl)-1-piperazinyl)ethyl]-4-methyl-2H-1-benzopyran-2-one Process A; starting materials: 3-[2-(methanesulphonyloxy)ethyl]- 6,7-dimethoxy-4-methyl-2H- 1-benzopyran-2-one (Example 28) and 1-(2-methoxyphenyl)piperazine hydrochloride; yield 14%; m.p. 174°–175° C. (from isopropanol).

Fumarate (x 0.5 $C_4H_4O_4$): process C; yield 72%; m.p. 227°–229° C. (from ethanol).

EXAMPLE 5

6-ethoxy-7-methoxy-4-methyl-3-[ 2-(4-phenyl-1-piperidinyl)ethyl] -2H-1-benzopyran-2-one Process A; starting materials: 6-ethoxy-3-[ 2-(methanesulphonyloxy)ethyl] - 7-methoxy-4-methyl-2H- 1-benzopyran-2-one (Example 29) and 4-phenylpiperidine; yield 69%; m.p. 195°–196° C. (from ethanol).

Fumarate: Process C; yield 61%; m.p. 235°–238° C. (from ethanol/water).

EXAMPLE 6

6-ethoxy-7-methoxy-4-methyl-3-[ 2-(4-phenyl-1-piperazinyl)ethyl]-2H-1-benzopyran-2-one Process B; starting materials: 6-ethoxy-3-[ 2-( methanesulphonyloxy)ethyl] -7-methoxy-4-methyl -2H- 1-benzopyran-2-one (Example 29) and 1-phenylpiperazine; yield 70%; m.p. 164°–165° C. (from isopropanol).

Fumarate: Process C; yield 96%; m.p. 202°–204° C. (from ethanol).

EXAMPLE 7

6-ethoxy-7-methoxy-3-{ 2-[ 4-(2-methoxyphenyl)-1-piperazinyl] ethyl}-4-methyl-2H-1-benzopyran-2-one Process A; starting materials: 6-ethoxy-3-[2-(methanesulphonyloxy)ethyl] - 7-methoxy-4-methyl-2H- 1-benzopyran-2-one (Example 29) and 1-(2-methoxyphenyl)piperazine; yield 54%; m.p. 143°–145° C. (from ethanol/chloroform).

Fumarate (x 0.5 $C_4H_4O_4$): process C; yield 83%; m.p. 185°–187° C. (from ethanol).

EXAMPLE 8

7-methoxy-3-{2-[ 4-(2-methoxyphenyl)-1-piperazinyl] ethyl}-4-methyl-6-(1-methylethoxy)-2H-1-benzopyran-2-one Process A; starting materials: 3-(2-chloroethyl)-7-methoxy- 4-methyl-6-(1-methylethoxy)-2H-1-benzopyran-2-one (Example 30) and 1-(2-methoxyphenyl)piperazine hydrochloride; yield 54%; m.p. 123°–125° C. (from ethanol).

Fumarate: Process C; yield 91%; m.p. 203°–205° C. (from ethanol/TBME).

EXAMPLE 9

6-(ethanesulphonyloxy)-7-methoxy-3-(2-[4-(2-methoxyphenyl]-1-piperazinyl]-ethyl)-4-methyl-2H-1-benzopyran-2-one Process A; starting materials: 3-(2-chloroethyl)-6-(ethanesulphonyloxy)-7-methoxy-4-methyl-2H-1-benzopyran-2-one (Example 31) and 1-(2-methoxyphenyl)piperazine; yield 34% of crystalline crude product.

Alternative process: 1.3 g (3.1 mmol) of 6-hydroxy-7-methoxy- 3-{2-[4-(2-methoxyphenyl)-1-piperazinyl]ethyl}-4-methyl- 2H-1-benzopyran-2-one (Example 2), two equivalents of sodium hydroxide and 2.5 equivalents of ethanesulphonic acid are dissolved in water/ethanol and stirred for 60 hours at room temperature. The reaction product is taken up in chloroform, washed with dilute sodium hydroxide and with water, dried over sodium sulphate, and the solvent is removed under reduced pressure. 0.94 g (59%) of pale yellow crystals with a melting point of 148°–150° C. (from ethanol/TBME) are obtained by column chromatography over silica gel (solvent: acetone/petroleum ether 1/1).

Fumarate (x −0.5 $C_4H_4O_4$): Process C; yield 79%; m.p. 94°–95° C. (from ethanol/TBME).

EXAMPLE 10

7,8-dimethoxy-3-{2-[4-(2-methoxyphenyl)-1-piperazinyl]ethyl}-4-methyl-2H-1-benzopyran-2-one Process A; starting materials: 3-(2-chloroethyl)- 7,8-dimethoxy-4-methyl-2H-1-benzopyran-2-one (Example 32) and 1-( 2-methoxyphenyl)piperazine hydrochloride; yield 6%; m.p. 146°–148° C. (from isopropanol/TBME).

Fumarate: Process C; yield 88%; m.p. 168°–170° C. (from acetone/petroleum ether/TBME).

EXAMPLE 11

7,8-diethoxy-3-{2-[4-(2-methoxyphenyl)-1-piperazinyl]ethyl}-4-methyl-2H-1-benzopyran-2-one Process B; starting materials: 3-(2-chloroethyl)-7,8-diethoxy- 4-methyl-2H-1-benzopyran-2-one (Example 33) and 1-(2-methoxyphenyl)piperazine; yield 13% of crude product.

Fumarate: process C; yield 89%; m.p. 175°–177° C. (from acetone).

EXAMPLE 12

5,6,7-trimethoxy-4-methyl-3-
[ 2-(4-phenyl-1-piperidinyl)ethyl] -
2H-1-benzopyran-2-one Process B; starting materials: 3-[ 2-( methanesulphonyloxy)ethyl] -5,6,7-trimethoxy-4-methyl-2H- 1-benzopyran-2-one (Example 34) and 4-phenylpiperidine; yield 27%; m.p. 117°–118° C. (from TBME/isopropanol).

Fumarate: Process C; yield 94%; m.p. 187°–189° C. (from acetone).

EXAMPLE 13

5,6,7-trimethoxy-4-methyl-3-
[ 2-(4-phenyl-1-piperazinyl)ethyl] -
2H-1-benzopyran-2-one Process B; starting materials: 3-[ 2-(methanesulphonyloxy)ethyl]- 5,6,7-trimethoxy-4-methyl-2H- 1-benzopyran-2-one (Example 34) and 1-phenylpiperazine; yield 49%; m.p. 136°–137° C. (from TBME/isopropanol).

Fumarate: Process C; yield 94%; m.p. 176°–178° C. (from acetone).

EXAMPLE 14

5,7-dimethoxy-4-methyl-3-
[ 2-(4-phenyl-1-piperidinyl)ethyl] -
2H-1-benzopyran-2-one Process B; starting materials: 3-[ 2-(methanesulphonyloxy)ethyl]- 5,7-dimethoxy-4-methyl-2H- 1-benzopyran-2-one (Example 35) and 4-phenylpiperidine; yield 18% of crude crystalline product.

Fumarate: Process C; yield 68%; m.p. 220°–222° C. (from isopropanol/TBME).

EXAMPLE 15

5,7-dimethoxy-4-methyl-3-[2-(4-phenyl-
1-piperazinyl)ethyl]- 2H-1-benzopyran-2-one Process B; starting materials: 3-[2-(methanesulphonyloxy)ethyl]- 5,7-dimethoxy-4-methyl-2H- 1-benzopyran-2-one (Example 35) and 1-phenylpiperazine; yield 50%; m.p. 112°–114° C. (from isopropanol/TBME).

Fumarate (x 0.5 $C_4H_4O_4$): process C; yield 91%; m.p. 216°–218° C. (from isopropanol/TBME).

EXAMPLE 16

5,7-dihydroxy-3-{2-[4-(2-methoxyphenyl)-
1-piperazinyl]ethyl}-
4-methyl-2H-1-benzopyran-2-one Process B; starting materials: 3-(2-chloroethyl)- 5,7-dihydroxy-4-methyl-2H-1-benzopyran-2-one (Example 36) and 1-( 2-methoxyphenyl)piperazine; yield 23% of crude crystalline product.

Fumarate (x 0.5 $C_4H_4O_4$): Process C; yield 80%; m.p. 225°–228° C. (from ethanol).

EXAMPLE 17

5,7-dimethoxy-3-{2-[ 4-(2-methoxyphenyl)-
1-piperazinyl] ethyl} -4-methyl
-2H-1-benzopyran-2-one Process B; starting materials: 3-[ 2-(methanesulphonyloxy)ethyl] -5,7-dimethoxy-4-methyl-2H- 1-benzopyran-2-one (Example 35) and 1-(2-methoxyphenyl)piperazine; yield 71%; m.p. 140°–142° C. (from ethanol).

Fumarate (x 0.5 $C_4H_4O_4$): Process C; yield 92%; m.p. 185°–188° C. (from ethanol).

EXAMPLE 18

5,7-diethoxy-3-{2-[4-(2-methoxyphenyl)-
1-piperazinyl]ethyl}-4-methyl-2H-1-benzopyran-2-one Process A; starting materials: 3-(2-chloroethyl)-5,7-diethoxy- 4-methyl-2H-1-benzopyran-2-one (Example 37) and 1-(2-methoxyphenyl)piperazine; yield 52% of oily crude product.

Fumarate (x 0.5 $C_4H_4O_4$): Process C; yield 26%; m.p. 210°–213° C. (from ethanol/water).

EXAMPLE 19

3-{2-[4-(2-methoxyphenyl)-1-piperazinyl]ethyl}-
4-methyl-5,7-dipropoxy-2H-1-benzopyran-2-one Process B; starting materials: 3-(2-chloroethyl)-4-methyl-5,7-dipropoxy-2H-1-benzopyran-2-one (Example 38) and 1-(2-methoxyphenyl)piperazine; yield 47% of crude product.

Fumarate: Process C; yield 49%; m.p. 178°–180° C. (from ethanol).

EXAMPLE 20

3-{2-[4-(2-ethoxyphenyl)-1-piperazinyl]ethyl}-
5,7-dimethoxy-4-methyl-2H-1-benzopyran-2-one Process B: starting materials: 3-(2-chloroethyl)- 5,7-dimethoxy-4-methyl-2H-1-benzopyran-2-one (Example 39) and 1-( 2-ethoxyphenyl)piperazine; yield 31% of crude product.

Fumarate: Process C; yield 87%; m.p. 205°–206° C. (decomposition; from acetone).

EXAMPLE 21

5,7-dimethoxy-4-methyl-3-{2-[4-(2-methylphenyl)-
1-piperazinyl]ethyl}-2H-1-benzopyran-2-one Process A; starting materials: 3-(2-chloroethyl)- 5,7-dimethoxy-4-methyl-2H-1-benzopyran-2-one (Example 39) and 1-( 2-methylphenyl)piperazine; yield 14% of oily crude product.

Fumarate (x 0.5 $C_4H_4O_4$): Process C; yield 57%; m.p. 218°–220° C. (from ethanol).

EXAMPLE 22

3-{2-[4-(2-fluorophenyl)-1-piperazinyl]ethyl}-5,7-dimethoxy-4-methyl-2H-1-benzopyran-2-one Process B; starting materials: 3-(2-chloroethyl)- 5,7-dimethoxy-4-methyl-2H-1-benzopyran-2-one (Example 39) and 1-( 2-fluorophenyl)piperazine; yield 42%; m.p. 152°–153° C. (from ethanol).

Fumarate: Process C; yield 93%; m.p. 237°–238° C. (decomposition; from acetone).

EXAMPLE 23

5,7-dimethoxy-4-methyl-3-{2-[ 4-(3-trifluoromethylphenyl)- 1-piperazinyl] ethyl}-2H-1-benzopyran-2-one Process B; starting materials: 3-(2-chloroethyl)- 5,7-dimethoxy-4-methyl-2H-1-benzopyran-2-one (Example 39) and 1-( 3-trifluoromethylphenyl)piperazine; yield 47%; m.p. 138°–139° C. (from isopropanol).

Fumarate: Process C; yield 88%; m.p. 224°–226° C. (from isopropanol/TBME).

EXAMPLE 24

3-[2-(4-hydroxy-4-phenyl-1-piperidinyl)ethyl]-5,7-dimethoxy-4-methyl-2H-1-benzopyran-2-one Process B; starting materials: 3-(2-chloroethyl)- 5,7-dimethoxy-4-methyl-2H-1-benzopyran-2-one (Example 39) and 4-hydroxy-4-phenylpiperidine; yield 41%; m.p. 177.5°–179° C. (from ethyl acetate/ethanol).

Fumarate (x 0.5 $C_4H_4O_4$): Process C; yield 60%; m.p. 218°–220° C. (from acetone/water).

EXAMPLE 25

3-{2-[4-(2-hydroxyphenyl)-1-piperazinyl]-ethyl}-5,7-dimethoxy-4-methyl-2H-1-benzopyran-2-one Process B; starting materials: 3-(2-chloroethyl)- 5,7-dimethoxy-4-methyl-2H-1-benzopyran-2-one (Example 39) and 1-( 2-hydroxyphenyl)piperazine; yield 22%; m.p. 164°–165° C. (from ethanol/TBME).

II EXAMPLES 26 TO 39 FOR INTERMEDIATE PRODUCES OF THE GENERAL FORMULA II

The following processes were used to prepare the compounds described in more detail in the following Examples 26 to 39:

Process D: A solution of 1.5 equivalents of methanesulphonic acid chloride in chloroform is added dropwise at 0° to 25° C. to the solution of the alcohol of the general formula IV appropriately substituted with $R^1$ to R4 and of 1.5 equivalents of triethylamine in chloroform, and the mixture is stirred for several minutes up to 16 hours at 0° to 25° C.

If the product precipitates it is suction filtered and if necessary washed with water. The chloroform solution is washed with water, dried with $Na_2SO_4$ then in a rotary evaporator, and if necessary chromatographed and recrystallised.

Process E: 2 to 4 equivalents of thionyl chloride are added dropwise while stirring to the alcohol of the general formula IV appropriately substituted with $R^1$ to $R^4$. The mixture is stirred for 1 to 20 hours at room temperature and water is then carefully added dropwise. The product precipitates, is suction filtered, and if necessary chromatographed and recrystallised.

EXAMPLE 26

3-[2-(methanesulphonyloxy)ethyl]-7-methoxy-4-methyl-2H-1-benzopyran-2-one

Process D; starting material: 3-(2-hydroxyethyl)-7-methoxy- 4-methyl-2H-1-benzopyran-2-one (Example 40); yield 82%; m.p. 174°–175° C. (from acetone).

EXAMPLE 27

3-(2-chloroethyl)-6-hydroxy-7-methoxy-4-methyl-2H-1-benzopyran-2-one

Process E; starting material: 6-hydroxy-3-(2-hydroxyethyl)- 7-methoxy-4-methyl-2H-1-benzopyran-2-one (Example 41); yield 98%; m.p. 230°–235° C. (from ethyl acetate/ethanol).

EXAMPLE 28

3-[2-(methanesulphonyloxy)ethyl]-6,7-dimethoxy-4-methyl-2H-1-benzopyran-2-one

Process D; starting material: 3-(2-hydroxyethyl)- 6,7-dimethoxy-4-methyl-2H-1-benzopyran-2-one (Example 42); yield 72%; m.p. 188°–191° C. (stirred out with TBME).

EXAMPLE 29

6-ethoxy-3-[2-(methanesulphonyloxy)ethyl]-7-methoxy-4-methyl-2H-1-benzopyran-2-one Process D; starting material: 6-ethoxy-3-(2-hydroxyethyl)- 7-methoxy-4-methyl-2H-1-benzopyran-2-one (Example 43); yield 94%; m.p. 153°–154° C. (stirred out with TBME).

EXAMPLE 30

3-(2-chloroethyl)-7-methoxy-4-methyl-6-(1-methylethoxy)-2H-1-benzopyran-2-one

Process E; starting material: 3-(2-hydroxyethyl)-7-methoxy- 4-methyl-6-(1-methylethoxy)-2H-1-benzopyran-2-one (Example44); yield 99%; m.p. 125°–127° C. (from ethanol).

EXAMPLE 31

3-(2-chloroethyl)-6-(ethanesulphonyloxy)-7-methoxy-4-methyl-2H-1-benzopyran-2-one One equivalent of sodium hydroxide is added to 7.0 g (26.1 mmol) of 3-(2-chloroethyl)-6-hydroxy-7-methoxy-4-methyl-2H- 1-benzopyran-2-one (Example 27) in 50 ml of water. The mixture is stirred for one hour at room temperature and 4.0 g (31.1 mmol) of ethanesulphonic acid chloride is then added dropwise.

The mixture is stirred for 20 hours at room temperature, a further 4.0 g (31.1. mmol) of ethanesulphonic acid chloride is added, and the mixture is stirred for a further 5 hours. The product is suction filtered and washed with water. Yield 5.5 g (59%); m.p. 154°–155° C. (from ethanol/petroleum ether).

EXAMPLE 32

3-(2-chloroethyl)-7,8-dimethoxy-4-methyl-2H-
1-benzopyran-2-one

Process E; starting material: 3-(2-hydroxyethyl)- 7,8-dimethoxy-4-methyl-2H-1-benzopyran-2-one (Example 45); yield 88%; m.p. 137°–139° C. (from isopropanol).

EXAMPLE 33

3-(2-chloroethyl)-7,8-diethoxy-4-methyl-2H-
1-benzopyran-2-one

Process E; starting material: 3-(2-hydroxyethyl)-7,8-diethoxy- 4-methyl-2H-1-benzopyran-2-one (Example 46); yield 85%; m.p. 89°–90° C. (from isopropanol).

EXAMPLE 34

3-[2-(methanesulphonyloxy)ethyl]-
5,6,7-trimethoxy-4-methyl-2H-1-benzopyran-2-one Process D; starting material: 3-(2-hydroxyethyl)- 5,6,7-trimethoxy-4-methyl-2H-1-benzopyran-2-one (Example 47); yield 84%; m.p. 114°–115° C. (from ethanol).

EXAMPLE 35

3-[2-(methanesulphonyloxy)ethyl]-5,7-dimethoxy-
4-methyl-2H-1-benzopyran-2-one

Process D; starting material: 3-(2-hydroxyethyl)- 5,7-dimethoxy-4-methyl-2H-1-benzopyran-2-one (Example 48); yield 92%; m.p. 170°–172° C. (from ethanol/chloroform).

EXAMPLE 36

3-(2-chloroethyl)-5,7-dihydroxy-4-methyl-2H-
1-benzopyran-2-one

Process E; starting material: 5,7-dihydroxy-3-( 2-hydroxyethyl)-4-methyl-2H-1-benzopyran-2-one (Example 49); yield 53%; m.p.218°–220° C. (x 1.0 acetone; from acetone/TBME/petroleum ether).

EXAMPLE 37

3-(2-chloroethyl)-5,7-diethoxy-4-methyl-2H-
1-benzopyran-2-one

Process E; starting material: 5,7-diethoxy-3-(2-hydroxyethyl)- 4-methyl-2H-1-benzopyran-2-one (Example 50); yield 83%; m.p. 123°–126° C. (from chloroform/ethanol).

EXAMPLE 38

5,7-bis(propyloxy)-3-(2-chloroethyl)-4-methyl-2H-
1-benzopyran-2-one

Process E; starting material: 5,7-bis(propyloxy)-3-( 2-hydroxyethyl)-4-methyl-2H-1-benzopyran-2-one (Example 51); yield 88%; m.p. 99°–101° C. (from isopropanol).

EXAMPLE 39

3-(2-chloroethyl)-5,7-dimethoxy-4-methyl-2H-
1-benzopyran-2-one

Process E; starting material: 3-(2-hydroxyethyl)- 5,7-dimethoxy-4-methyl-2H-1-benzopyran-2-one (Example 48); yield 73%; m.p. 129°–130° C. (from isopropanol).

III EXAMPLES 40 TO 52 FOR INTERMEDIATE PRODUCTS OF THE GENERAL FORMULA IV

The following processes were used to prepare the compounds described in more detail in the following Examples 40 to 52:

Process F: The phenol of the general formula V appropriately substituted with $R^1$ to $R^3$ is suspended in about 4 to 6 times the amount by weight of 75% aqueous sulphuric acid. 1 equivalent of 2-acetyl-γ-butyrolactone is added dropwise at 0° to 25° C. while stirring, and the mixture is stirred for a further 1 to 18 hours at room temperature and then diluted with ice/water. If the product separates out as a solid precipitate it is stirred if necessary for several hours at room temperature, suction filtered, washed with water, dried under reduced pressure and recrystallised. Otherwise it is extracted with chloroform, the organic phase is washed with water, dried with $Na_2SO_4$ and then in a rotary evaporator, and if necessary chromatographed and recrystallised.

EXAMPLE 40

3-(2-hydroxyethyl)-7-methoxy-4-methyl-2H-
1-benzopyran-2-one

Process F; starting material: 3-methoxyphenol; yield 16%; m.p. 141°–142° C. (from isopropanol/TBME).

EXAMPLE 41

6-hydroxy-3-(2-hydroxyethyl)-7-methoxy-4-methyl-
2H-1-benzopyran-2-one

Process F; starting material: methoxyhydroquinone; yield 54%; m.p. 229°–235° C. (from methanol).

EXAMPLE 42

3-(2-hydroxyethyl)-6,7-dimethoxy-4-methyl-2H-
1-benzopyran-2-one 40.0 g (160 mmol) of 6-hydroxy-3-(2-hydroxyethyl)-7-methoxy- 4-methyl-2H-1-benzopyran-2-one (Example 41), 45.4 g (320 mmol) of methyl iodide and 66.3 g (480 mmol) of potassium carbonate in 500 ml of DMF are stirred for 22 hours at 60° to 80° C. The reaction solution is evaporated, extracted with chloroform, and the organic phase is washed with dilute sodium hydroxide and with water, dried with $Na_2SO_4$, and re-evaporated. Yield 31.6 g (75%); m.p. 184°–187° C. (from isopropanol).

EXAMPLE 43

6-ethoxy-3-(2-hydroxyethyl)-7-methoxy-4-methyl-2H-
1-benzopyran-1-one 4.72 g (118 mmol) of sodium hydride (60% in white oil) is freed from the oil, suspended in 100 ml of DMF, and a solution of 26.8 g (107 mmol) of 6-hydroxy-3-(2-hydroxyethyl)- 7-methoxy-4-methyl-2H-1-benzopyran-2-one (Example 41) in 500 ml of DMF is added dropwise at room temperature. 25.1 g (161 mmol) of ethyl iodide is added after 30 minutes and the mixture is stirred for 14 hours at 80° to 90° C. The solution is evaporated, extracted with chloroform, and the organic phase is washed with dilute sodium hydroxide and with water, dried with $Na_2SO_4$ and re-evaporated. Yield 25.1 g (84%); m.p. 156°–157° C. (from isopropanol).

EXAMPLE 44

3-(2-hydroxyethyl)-7-methoxy-4-methyl-6-(1-methylethoxy)-2H-1-benzopyran-2-one 67 g (268 mmol) of 6-hydroxy-3-(2-hydroxyethyl)-7-methoxy- 4-methyl-2H-1-benzopyran-2-one (Example 41) is carefully added, using an ice bath for cooling, to 11.8 g (295 mmol) of sodium hydride (60% in white oil) in 300 ml of DMF. The mixture is stirred for 1 hour at room temperature, and then 49.5 g (402 mmol) of 2-bromopropane is added dropwise and the mixture is stirred for 24 hours at 60° C. under nitrogen. After adding a further 3.33 g (83 mmol) of sodium hydride and 52.4 g (426 mmol) of 2-bromopropane, the mixture is stirred for a further 24 hours at 60° C. The solution is evaporated, extracted with ethyl acetate, and the organic phase is washed with water, dried with $Na_2SO_4$ and re-evaporated. The product is purified by column chromatography over silica gel 60 (eluent: ethyl acetate). Yield 53.3 g (68%); m.p. 110°–112° C. (from acetone/PE).

EXAMPLE 45

3-(2-hydroxyethyl)-7,8-dimethoxy-4-methyl-2H-1-benzopyran-2-one 18.4 g (279 mmol) of potassium hydroxide (85%) and 30.0 g (127mmol) of 7,8-dihydroxy-3-(2-hydroxyethyl)-4-methyl-2H- 1-benzopyran-2-one (Example 52) are stirred in 700 ml of ethanol for 30 minutes at room temperature. 39.7 g (280 mmol) of methyl iodide is added and the mixture is stirred for 32 hours at 60° C. After adding a further 2.11 g (32 mmol) of potassium hydroxide and 4.54 g (32 mmol) of methyl iodide, the mixture is stirred for a further 8 hours at 60° C. The solution is evaporated, extracted with chloroform, and the organic phase is washed with water, dried with $Na_2SO_4$ and re-evaporated. Yield 16.15 g (48%); m.p. 113°–114° C. (from TBME/isopropanol).

EXAMPLE 46

7,8-diethoxy-3-(2-hydroxyethyl)-4-methyl-2H-1-benzopyran-2-one 30.0 g (127 mmol) of 7,8-dihydroxy-3-(2-hydroxyethyl)-4-methyl-2H-1-benzopyran-2-one (Example 52), 52.7 g (381 mmol) of potassium carbonate and 43.6 g (280 mmol) of ethyl iodide are stirred under reflux for 50 hours in 800 ml of ethanol. The solution is evaporated, extracted with chloroform, and the organic phase is washed with water, dried with $Na_2SO_4$, and re-evaporated. Yield 21.0 g (57%); m.p. 130°–131° C. (from isopropanol).

EXAMPLE 47

3-(2-hydroxyethyl)-5,6,7-trimethoxy-4-methyl-2H-1-benzopyran-2-one

Process F; starting material: 3,4,5-trimethoxyphenol; yield 29%; m.p. 95°–97° C. (from petroleum ether/TBME).

EXAMPLE 48

3-(2-hydroxyethyl)-5,7-dimethoxy-4-methyl-2H-1-benzopyran-2-one

Process F; starting material: 3,5-dimethoxyphenol; yield 72%; m.p. 128°–130° C. (from isopropanol/TBME).

Alternative method: 100.0 g (423 mmol) of 5,7-dihydroxy-3-( 2-hydroxyethyl)-4-methyl-2H-1-benzopyran-2-one (Example 49), 175.5 g (1270 mmol) of potassium carbonate and 150.2 g (1058 mmol) of methyl iodide are stirred under reflux for 4 hours in 1800 ml of ethanol. The solution is filtered, evaporated, extracted with chloroform, and the organic phase is washed with water, dried with $Na_2SO_4$ and re-evaporated. Yield 49.3 g (44%); m.p. 148°–150° C. (from isopropanol/TBME).

EXAMPLE 49

5,7-dihydroxy-3-(2-hydroxyethyl)-4-methyl-2H-1-benzopyran-2-one

Process F; starting material: phloroglucin dihydrate; yield 88%; m.p. 243°–245° C. (from ethanol/water).

EXAMPLE 50

5,7-diethoxy-3-(2-hydroxyethyl)-4-methyl-2H-1-benzopyran-2-one 33.0 g (140 mmol) of 5,7-dihydroxy-3-(2-hydroxyethyl)-4-methyl-2H-1-benzopyran-2-one (Example 49), 56.0 g (560 mmol) of potassium bicarbonate and 76.4 g (490 mmol) of ethyl iodide are stirred in 500 ml of DMF for 55 hours at 80° C. under nitrogen. The solution is evaporated, extracted with chloroform, and the organic phase is washed with dilute sodium hydroxide and with water, dried with $Na_2SO_4$ and re-evaporated. The product is purified by column chromatography over silica gel 60 (eluent: ethylacetate/acetone). Yield 19.5 g (48%); m.p. 117°–119° C. (from acetone/petroleum ether).

EXAMPLE 51

5,7-bis(propyloxy)-3-(2-hydroxyethyl)-4-methyl-2H-1-benzopyran-2-one 30.0 g (127 mmol) of 5,7-dihydroxy-3-(2-hydroxyethyl)-4-methyl-2H-1-benzopyran-2-one (Example 49), 50.8 g (507 mmol) of potassium bicarbonate, 54.7 g (445 mmol) of 1-bromopropane and 5.0 g of potassium iodide are stirred in 500 ml of DMF for 43 hours at 80° C. The solution is evaporated, extracted with chloroform, and the organic phase is washed with water, dried with $Na_2SO_4$ and re-evaporated. The product is purified by column chromatography over silica gel 60 (eluent: ethyl acetate/petroleum ether 9/1). Yield 28.8 g (71%); m.p. 106°–108° C. (from petroleum ether/acetone).

EXAMPLE 52

7,8-dihydroxy-3-(2-hydroxyethyl)-4-methyl-2H-1-benzopyran-2-one

Process F; starting material: pyrogallol; yield 66%; m.p. 221°–222° C. (from ethanol/water).

PHARMACOLOGICAL INVESTIGATIONS

The following method was used to determine the neuroprotective/anticonvulsive activity of the compounds according to the invention of the general formula I:

In order to evaluate the neuroprotective activity, NMDA was administered intravenously in an amount of 25 mg/kg/ 10 ml to male NMRI mice having a body weight of 20–25 g. As a result of this administration the animals suffered clonic and in some cases also tonic convulsions, leading to death. Prevention of death is used as a criterion of the effectiveness of the investigated compounds.

All experimental animals had free access to food and water before the experiments. The test and reference substances were administered orally as a suspension in 0.2% agar or water, by means of a pharyngeal probe, in some cases with the aid of solubilizers such as PEG-400. Control animals received the same volume of solvents, if necessary with the addition of solubilizers. One hour after administration of the substance NMDA was administered intravenously and the occurrence of convulsions was observed.

The results of the tests carried out (NMDA 25 mg i.v.) at doses of 5 mg of the compounds according to the invention per kg body weight compared to known NMDA antagonists are given in Table 1. The percentage proportion of the surviving animals is given as % effect.

Table 1 also gives as ED-50 values those doses of the substances according to the invention and other NMDA antagonists, which in the NMDA i.v. test (25 mg/kg) one hour after administration protected 50% of the animals against NMDA-induced death.

The ED-50 values were determined according to the method of Lichtfield and Wilcoxon, J. Pharmacol. exp. Therapeut. 96, 99 (1949), in each case using 4–5 groups of animals each containing 10 animals per dose stage.

Throughout the course of the experiment the animals were observed for signs of substance-induced behavioural changes and neurotoxicity. No signs of an intrinsic toxic effect were observed with all the compounds according to the invention in the doses employed.

TABLE 1

Results of the NMDA test (25 mg/kg i.v.) and the ED-50 values

| Substance according to example No. | Dose (mg/kg oral) 1 hr before test | Number of animals in the experiment | Protective action (%) | ED-50 (mg/kg oral) |
|---|---|---|---|---|
| 1 | 5 | 8 | 87.5 | 0.8 |
| 2 | 5 | 8 | 100 | 0.2 |
| 3 | 5 | 8 | 50 | |
| 4 | 5 | 8 | 100 | 0.4 |
| 5 | 5 | 8 | 75 | 4.1 |
| 6 | 5 | 8 | 87.5 | 2.0 |
| 7 | 5 | 8 | 100 | 0.4 |
| 8 | 5 | 8 | 100 | 0.7 |
| 9 | 5 | 8 | 100 | 0.6 |
| 10 | 5 | 8 | 100 | 0.4 |
| 11 | 5 | 8 | 100 | |
| 12 | 5 | 8 | 75 | 3.4 |
| 13 | 5 | 8 | 62.5 | |
| 14 | 5 | 8 | 87.5 | 2.2 |
| 15 | 5 | 8 | 87.5 | 1.0 |
| 16 | 5 | 8 | 100 | 0.2 |
| 17 | 5 | 8 | 100 | 0.2 |
| 18 | 5 | 8 | 100 | 0.6 |
| 19 | 5 | 8 | 100 | |
| 20 | 5 | 8 | 100 | |
| 21 | 5 | 8 | 87.5 | |
| 22 | 5 | 8 | 100 | |
| 23 | 5 | 8 | 25 | |
| 24 | 5 | a | 25 | |
| 25 | 5 | 8 | 87.5 | |
| Flunarizin | 50 | 8 | 100 | 22.8 |
| Nimodipin | 20 | 8 | 87.5 | 18.5 |
| Verapamil | 20 | 8 | 87.5 | 17.3 |
| Dextromethorphan | 50 | 8 | 50 | 66.7 |
| Ketamin | 20 | 8 | 0 | |

EXAMPLES OF THE PREPARATION OF PHARMACEUTICAL FORMULATIONS OF THE SUBSTANCES ACCORDING TO THE INVENTION

A. Tablets:

The following constituents are required to make tablets containing 5–250 mg of active component, depending on the desired effect

| | |
|---|---|
| Substance according to the invention | 200 to 5 000 g |
| Cellulose powder | 2 000 g |
| Maize starch | 1 200 g |
| Colloidal silicic acid | 80 g |
| Magnesium stearate | 20 g |
| Lactose | to make up to 10 000 g |

The active component is triturated if necessary, homogeneously mixed with the excipients, and pressed in the usual way into tablets each weighing 250 mg and 9 mm in diameter. With dosages above 125 mg tablets each weighing 500 mg and 11 mm in diameter are pressed. If desired, the tablets are provided with a film coating.

B. Capsules:

The following constituents are required to make capsules containing 5–250 mg of active component, depending on the desired effect

| | |
|---|---|
| Substance according to the invention | 500 to 12 500 g |
| Maize starch | 2 000 g |
| Colloidal silicic acid | 300 g |
| Magnesium stearate | 50 g |
| Cellulose powder | to make up to 20 000 g |

The finely powdered substances are homogeneously mixed and added to hard gelatin capsules of size 2 in an amount of 200 mg per capsule, or in the case of dosages above 125 mg, are added to hard gelatin capsules of size 0 in an amount of 400 mg per capsule.

We claim:

1. A 2H-1-benzopyran-2-one having of the formula I,

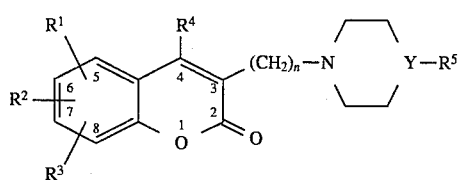

wherein:

- $R^1$ is a hydroxy radical, an alkoxy radical with 1 to 5 C atoms, a cycloalkoxy radical with 4 to 6 C atoms, or an alkyl- or arylsulphonyloxy radical $R^6—SO_2O—$,
- $R^2$ and $R^3$ are, independently of one another, a hydrogen atom, hydroxy radical, alkoxy radical with 1 to 4 C atoms, or a cycloalkoxy radical with 4 to 6 C atoms,
- $R^4$ is a hydrogen atom, an alkyl group with 1 to 4 C atoms, or a phenyl radical,
- Y is a nitrogen atom, a CH group or a COH group,
- $R^5$ is a phenyl, naphthyl, pyridinyl or pyrimidinyl radical, which is optionally substituted with in each case one or two $C_1-C_5$ alkyl groups, with in each case one or two halogen atoms, with halogen and simultaneously $C_1-C_5$ alkyl, with perfluoroalkyl with 1 to 3 C atoms, $C_1-C_5$ alkoxy, hydroxy, methylenedioxy or nitro,
- $R^6$ is an alkyl radical with 1 to 5 C atoms, a cycloalkyl radical with 4 to 6 C atoms or a phenyl radical, which is optionally substituted with in each case one or two $C_1-C_5$ alkyl groups, with in each case one or two halogen atoms or with perfluoroalkyl with 1 to 3 C atoms, and
- n is an integer from 1 to 4;

or pharmaceutically compatible acid addition salts thereof, with the exception however of 7,8-dimethoxy-4-methyl-3-[(4-phenyl-1-piperazinyl)methyl]-2H- 1-benzopyran-2-one.

2. A compound according to claim 1, wherein in said formula I

- $R^1$ is a hydroxy, methoxy, ethoxy, propyloxy or ethane sulphonyloxy radical,
- $R^2$ and $R^3$ are, independently of one another, a hydrogen atom, a hydroxy or alkoxy radical with 1 to 3 C atoms,
- $R^4$ is a methyl group,
- Y is a nitrogen atom, a CH group or a COH group,
- $R^5$ is a phenyl radical optionally substituted with hydroxy, methoxy, ethoxy, methyl, fluoro or trifluoromethyl, and
- n=2 and the addition compounds thereof with physiologically compatible acids.

3. A pharmaceutical preparation comprising a pharmaceutically effective amount of at least one compound as claimed in claim 1 or claim 2, together with a pharmaceutically acceptable carrier.

* * * * *